United States Patent [19]

Patel

[11] Patent Number: 5,366,502
[45] Date of Patent: Nov. 22, 1994

[54] SUPPLEMENTARY INTRAOCULAR LENS SYSTEM

[75] Inventor: Anilbhai Patel, Seattle, Wash.

[73] Assignee: Nestle S.A., Vevey, Switzerland

[21] Appl. No.: 168,563

[22] Filed: Dec. 16, 1993

Related U.S. Application Data

[63] Continuation of Ser. No. 72,362, Jun. 4, 1993, which is a continuation of Ser. No. 956,450, Oct. 2, 1992, abandoned, which is a continuation of Ser. No. 859,640, Mar. 23, 1992, abandoned, which is a continuation of Ser. No. 653,863, Feb. 8, 1991, abandoned, which is a continuation of Ser. No. 344,705, Apr. 28, 1989, abandoned.

[51] Int. Cl.$^5$ .............................................. A61F 2/16
[52] U.S. Cl. .................................................... 623/6
[58] Field of Search ........................................ 623/6

[56] References Cited

U.S. PATENT DOCUMENTS 4,892,543  1/1990  Turley ................................. 623/6
5,201,762  4/1993  Hauber ................................ 623/6

FOREIGN PATENT DOCUMENTS 0194390  9/1986  European Pat. Off. ............. 623/6
3626869  2/1988  Germany ............................ 623/6

*Primary Examiner*—David H. Willse
*Attorney, Agent, or Firm*—Sally S. Yeager; Jeffrey S. Schira

[57] ABSTRACT

A supplemental intraocular lens is provided for either preoperative or postoperative attachment to a conventional implanted intraocular lens to provide an adjustable or removable multi-focal optic or to provide a necessary optic of spherical, cylindrical or combination shape for refractive error correction in aphakic patients. An intraocular lens system is also provided including a primary intraocular lens modified to provide for securing a supplemental corrective intraocular lens to the primary lens. Either the primary or supplemental lens could be formed of a suitable multi-focal lens, or both lenses could be mono-focal.

8 Claims, 9 Drawing Sheets

  
*FIG 2A*  *FIG 2B*  *FIG 2C*
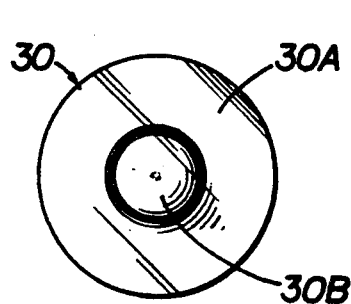 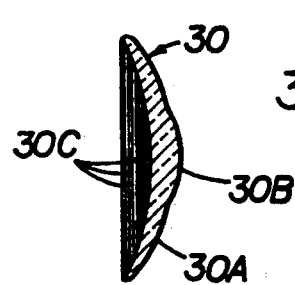 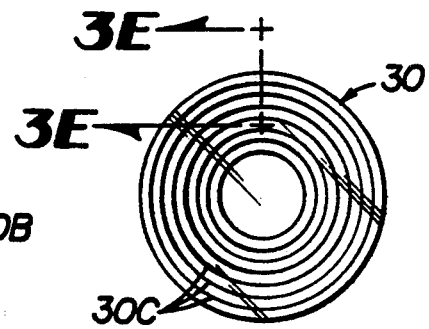
*FIG 3A*  *FIG 3B*  *FIG 3C*
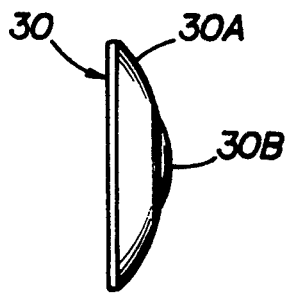 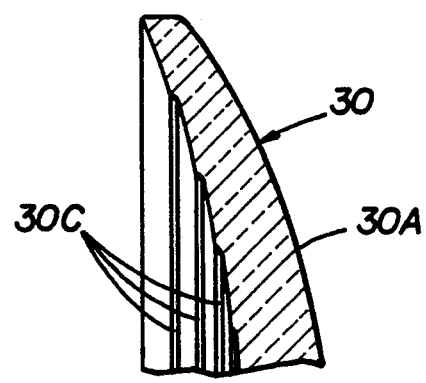
*FIG 3D*  *FIG 3E*

SUPPLEMENTARY INTRAOCULAR LENS SYSTEM

This is a continuation of application Ser. No. 08/072,362, filed Jun. 4, 1993 (currently pending), which is continuation of application Ser. No. 07/956,450, filed Oct. 2, 1992 (abandoned), which is continuation of application Ser. No. 07/859,640, filed Mar. 23, 1992 (abandoned), which is continuation of application Ser. No. 07/653,863, filed Feb. 8, 1991 (abandoned), which is continuation of application Ser. No. 07/344,705, filed Apr. 28, 1989 (abandoned).

BACKGROUND OF THE INVENTION

1. Field of the Invention

This invention relates generally to the field of intraocular lenses (IOLs) and, more particularly, to IOL's having changeable refractive correction after initial implantation into the eye.

2. General Background

The human eye in its simplest terms functions to provide vision by transmitting an image through a clear outer portion called the cornea, and focusing the image by way of a lens onto a retina. The quality of the focused image depends on many factors including the size and shape of the eye, and the transparency of the cornea and lens.

When age or disease causes the lens to becomes less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens or IOL. Patients having such removal are referred to as aphakic patients.

Because removal of the lens leaves the eye with no ability to focus an image on the retina, aphakic patients require a substitute for the removed lens. Spectacles, contact lenses and surgical implantation of an intraocular lens or IOL are the three presently known techniques for providing this function. Surgically implanted IOLs are preferable to spectacles or contact lenses in that they provide a permanent replacement for the removed lens. However, because it is surgically implanted, the corrective power of the IOL cannot be as easily changed as the external spectacles or contact lens alternatives.

As presently practiced, cataract removal and the implantation of a replacement IOL is accomplished in a single surgical procedure through an incision in the cornea. The incision needed for cataract removal depends upon the method of cataract removal and ranges from 3.0 to 12.0 mm. A conventional hard lens can be inserted through an incision that is about 7 mm or larger. IOLs formed of soft or foldable materials can be inserted through smaller openings.

In addition, IOLs also include haptics or support loops for holding the IOL in place in the eye. The haptics are generally in the form of at least two relatively flexible, elongated, open-ended loops that project from the edge of an optic portion. These haptics may also require additional incision length, depending upon their length and configuration.

IOLs are available in a range of corrective refractive powers. Prior to surgery, the physician can take various measurements and use one of several proposed formulae to determine IOL power to achieve the desired post-operative refraction needs of the patient. The physician then selects an intraocular lens nearest to the determined IOL power lens within a wide range of diopter powers.

However, this procedure which determines the post-operative refraction of the patient is difficult and inexact. Although there have been several formulae used for determining the approximate power of the lens for achieving desired refraction for a particular patient, they are not totally exact, and involve measurement of the axial length of the eye, corneal power measurement, and assume lack of post-operative induced astigmatism or spherical refractive changes in the cornea.

Examples of several formulae used for calculating IOL power needed for desired post-operative refractive requirements for aphakic patients are presented in an article by Scott C. Richards, et al, entitled "Clinical Evaluation Of Six Intraocular Lens Calculation Formulas" A. Intraocular Implant Soc. J., Vol. 11, March, 1985, pp. 153-158. Errors in measurement, inaccuracy of assumptions, and the difficulty of achieving precise placement of an IOL, make it unlikely that an IOL with an exact corrective power can be predicted. This in turn can lead to residual refractive errors and the need to correct the power of the IOL after initial surgery.

In addition to the inherent measurement problems, post-operative changes can occur which also change the refractive power needed for an IOL in a particular patient. Such post-operative change commonly occurs in very young aphakic patients because the size and shape of an eye changes with maturity. It can also occur as a result of differences in the manner in which the capsular bag shrinks, an IOL moves, or a cornea incision heals in different patients and even suturing techniques of different physicians.

Surgical implantation of an IOL involves inserting a lens through the cataract removal incision and then manipulating the lens into position in either the anterior or posterior chamber of the eye such that the support loops or haptics are properly placed. Proper placement and securing of the IOL requires manipulation of the lens in a way that could involve contact with the iris, cornea or other sensitive internal tissues. This manipulation adds to the trauma of the cataract surgical procedure.

Although the benefits to a patient of having a permanently implanted lens substitute far outweigh any risks involved in the trauma associated with cataract surgery, a second surgical procedure to remove an IOL and replace it with a properly powered one adds another undesirable level of trauma and risk. In addition, an IOL that has been in place for some time could have support loops that are encapsulated in the eye by tissue adhesions and may be difficult to remove. For these reasons, it would be desirable to be able to change the power of an IOL without removing the original implanted IOL.

Several patents relate to altering the refractive power of implanted IOL's, as follows: U.S. Pat. No. 4,685,922, issued to Peyman, describes one technique for altering the refractive power of an IOL by providing rupturable fluid-fill membrane sections in the implant. U.S. Pat. No. 4,685,921, issued to Peyman, describes another technique providing expandable chambers in the implant.

The techniques in both of these patents are limited by their design to correction of spherical refractive error as they can only provide changes along the axial length of the eye and are not able to correct cylindrical errors commonly occurring as a result of post-operative astigmatism in aphakic patients.

U.S. Pat. No. 4,575,373, issued to Johnston, describes a method of using a laser to heat shrink an outer portion of an IOL to alter its shape and change its corrective power. Again, the alteration in lens shape is limited to alterations in the axial direction and cannot be used in making cylindrical error corrections.

The only known technique for correcting cylindrical errors is either to remove and replace the original IOL or to add correction by way of spectacles or contact lenses.

It would therefore be desirable to be able to alter the corrective power of an implanted intraocular lens to compensate for both spherical and cylindrical refractive errors with a minimum of trauma and to avoid the need for complete removal of the original IOL or the use of supplemental external correction such as spectacles or contact lens.

Another relatively recent development is the use of bifocal or other multi-focal IOLs where two or more optical zones are incorporated into the optic portion of an IOL. This feature has the advantage of eliminating the need for contact lenses or spectacles for an IOL wearer because of the inability of IOLs to accommodate and focus properly on images at different distances. Several articles have reported different approaches to multi-focal lens design and some initial observations or advantages of the use of diffractive optics where light is spread through multiple, sub-millimeter edges, as compared with refractive optics where light is bent as it passes through separate optic zones of different diopter powers. See Futhey, John, "New IOL Utilizes Diffractive Optics to Focus Near, Distance" and Akashi, Ronald, "Diffractive IOL Design Pick Ups Where Bifocal Contact Lens Principles Left Off," Symposium Highlights, Supplement Two Ocular Surgery News, Sep. 15, 1988.

While the IOL industry is optimistic about the efficacy of multi-focal IOLs, preliminary results indicate that a relatively small but significant segment of IOL patients cannot tolerate or accept bifocal or multi-focal IOLs and require mono-focal IOLs. Other factors can affect whether a multi-focal IOL is useful such as, for example, glare caused by a tilted lens, fluctuation in vision because of small pupil size caused by severe decentralization, and surgically-induced astigmatism which reduces the effectiveness of a multi-focal lens.

When a multi-focal IOL is implanted which cannot be tolerated by the patient or is not properly focused, the surgeon has to remove the entire IOL and replace it with another one, with the undesirable consequences described above.

SUMMARY OF THE INVENTION

The subject invention relates to an IOL system for correcting refractive errors in aphakic patients. The invention includes a primary IOL (PIOL) and a supplemental IOL (SIOL) having a predetermined refractive power or in the form of a multi-focal IOL, which combines with the refractive power of an implanted primary IOL (PIOL) to provide a composite IOL that suits the particular patient.

After the PIOL is implanted, a determination is made whether its focusing ability is satisfactory or whether its diopter power needs to be changed. If change is required, an SIOL is implanted through an incision smaller than the one required by the PIOL.

The PIOL can also be combined with an SIOL in the form of a multi-focal optic, either at the time of initial implant or later, to determine whether the patient can tolerate a multi-focal lens or whether the particular multi-focal lens is suitable. If the multi-focal SIOL is not suitable it can be removed or replaced more easily than if the multi-focal lens was a conventional IOL.

The SIOL includes connectors for mating the supplemental lens to the implanted PIOL. The connectors can be in the form of hooks, projections, slots, loops or the like, which are suitable for securing the SIOL to the PIOL. The PIOL would be likewise adapted to receive and mate with the SIOL to form the desired composite IOL.

Accordingly, the present invention provides a system that includes an SIOL for correcting the focusing ability and the diopter power of an implanted PIOL or provides an adjustable or removable multi-focal optic scheme. The SIOL could also be a multi-focal lens. The SIOL in any form is connected to an implanted PIOL for changing the diopter power of the PIOL in order to enhance its focusing ability.

BRIEF DESCRIPTION OF THE DRAWINGS

A better understanding of the invention can be obtained when the detailed description of exemplary embodiments set forth below is considered in conjunction with the appended drawings, in which:

FIGS. 2A-2C are schematic views of different configurations of primary and supplemental IOLs;

FIGS. 3A-3B are front and side elevation views, respectively, of one embodiment of a refractive multi-focal IOL;

FIGS. 3C, 3D and 3E are front and side elevation views and a segment view, respectively, of one embodiment of a refractive/diffractive multi-focal IOL;

DETAILED DESCRIPTION OF THE EXEMPLARY EMBODIMENT

Figure 1B:
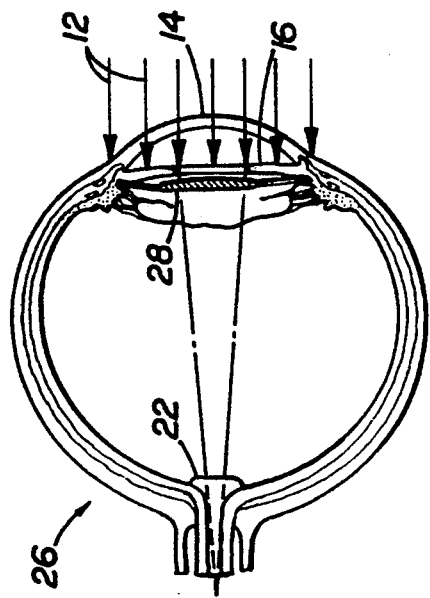
FIGS. 1B-1C illustrate the eye of FIG. 1A with the natural lens removed and a typical primary IOL (posterior and anterior chambers respectively) in place, illustrating in particular an unfocused image on the retina.
Figure 1D:
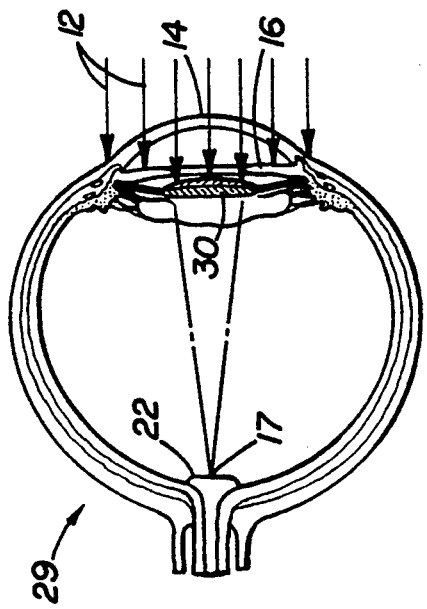
FIG. 1D is a view similar to FIG. 1A illustrating a supplemental IOL connected to the primary IOL shown in FIG. 1B.
Figure 1A:
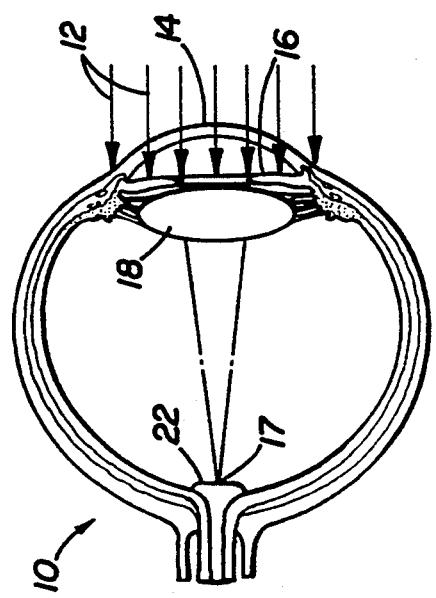
FIG. 1A is a schematic cross-section view of a normal eye, illustrating in exaggerated fashion an image focused on the retina.

FIG. 1A illustrates schematically in cross-section a normal eye 10 and the optics involved in focusing an image on a retina designated by reference numeral 22. As shown, an incoming image, in the form of arrows designated by reference numeral 12, enters the eye 10 through a cornea 14, passes through a pupil formed by an iris 16, and is focused onto the retina 22 at 17 by a natural lens 18.

Figure 1C:
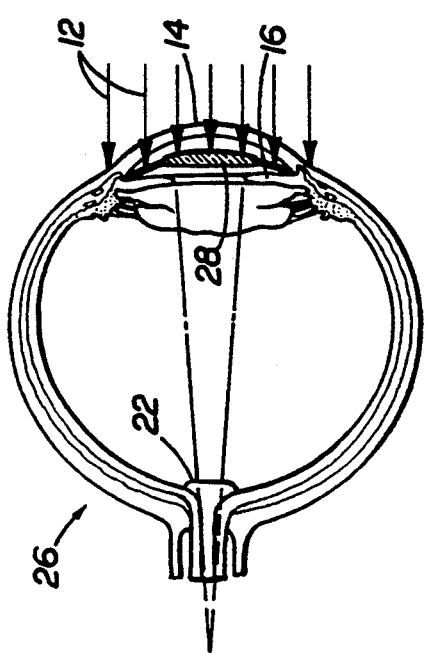

FIG. 1B illustrates in similar fashion an aphakic eye 26 in which a primary IOL 28 (PIOL) has been implanted to replace a natural lens (not shown) through the same incision (not shown) through which the natural lens was removed. As illustrated in exaggerated form in FIG. 1B, the diopter power of the PIOL can be incorrect so that the incoming image 12 is not satisfactorily focused on the retina 22. Instead, the image is focused behind the retina as shown. The PIOL 28 can be implanted in the posterior chamber as shown in FIG. 1B or in the anterior chamber as shown in FIG. 1C.

FIG. 1D illustrates schematically an aphakic eye 29 in which, in accordance with the present invention, the PIOL 28 is implanted in the posterior chamber and a supplemental IOL (SIOL) 30 has been mounted on the anterior surface of the PIOL 28 in order to correct the diopter power of the PIOL and provide the proper focusing ability for the composite lens. This is illustrated in FIG. 1D by showing the incoming image 12 properly focused at 17 on the retina 22, similar to the image formed by the natural lens 18 in FIG. 1A.

Since a power for the PIOL prior to its implantation is computed by the operating physician based on a number of manually measured parameters, with varying degrees of accuracy, oftentimes the computed power is not correct. Also, the final axial position of the PIOL is not exactly predictable and hence the selection formulas do not give totally accurate and predictable refraction. An SIOL 30 can be chosen after the PIOL 28 has been implanted, based on the patient's need for correction after the healing process following the PIOL implant is relatively complete.

The power of the SIOL 30, being supplemental, will be small, typically in the range of about −6 to +6 diopters. The SIOL 30 can therefore be made of one of the so-called "soft" materials such as a silicone, acrylic, hydrogel or the like, which has a relatively high refractive index and can be folded for insertion using a suitable insertion tool. Such a technique is known in the art for insertion of primary IOLs formed of such soft materials, which requires a much smaller incision than normally used in the implantation of the primary IOL. For an SIOL 30 formed of one of the "soft" materials, an incision smaller than the initial corneal incision would need be reopened, thus minimizing trauma to the aphakic eye 26.

However, the SIOL could also be formed of one of the stiff plastics such as PMMA and be easily implanted through the same incision required for PIOL because the SIOL would have a smaller thickness due to its relatively low diopter power as mentioned above.

The PIOL and SIOL can be of any suitable shape such as, for example, bi-convex, plano-convex, convex-concave. Various combinations of possible PIOL and SIOL configurations are shown schematically in FIGS. 2A–2C. As shown, the adjacent surfaces of the PIOLs 28 and SIOLs 30 can either be in contact with each other or spaced apart.

Further, as mentioned above, the SIOL can be of a multi-focal design so that it can easily be replaced with another multi-focal lens more suitable to the patient or with a mono-focal design if the patient cannot tolerate a multi-focal lens. The multi-focal SIOL 30 can be of any suitable bifocal design such as, for example, a refractive lens of the type shown in FIGS. 3A–3B where a peripheral portion 3A is used for distance vision and a central add portion 30B is used as a near vision zone. Other suitable configurations could also be used (not shown).

Another type of multi-focal SIOL 30 could be used such as shown in FIGS. 3C, 3D and 3E, which utilize a refractive/diffractive principle. Bifocal vision is achieved by a defractive optical system formed on the concave posterior surface of the SIOL 30 which includes a large number of concentric annular zones 30C with small, wedge-like tiers 30D at the border of each zone. Subsequent to refraction by the lens body, each tier 30D diffracts light into two different foci for near and far. Other suitable diffractive designs could also be used (not shown).

Alternatively, the PIOL 28 could be formed of a multi-focal lens of types shown in FIGS. 3A–3E or other designs. In this embodiment, the SIOL 30 could be used to provide the proper, corrective diopter power for the composite.

FIGS. 4–31 illustrate various embodiments of primary and supplemental IOLs formed in accordance with the present invention. Although each of the embodiments illustrates the PIOL and SIOL as a mono-focal lens of a particular shape, it should be understood that they can be formed of other suitable shapes and combinations of mono-focal and/or multi-focal designs.

Figure 4:
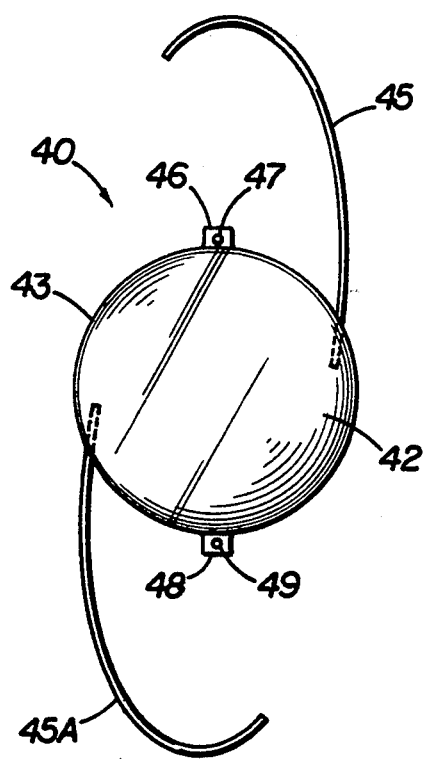
FIG. 4 is a front elevational view of a primary IOL modified in accordance with one embodiment of the invention, including mating members for securing a supplemental IOL to the primary IOL.
Figure 5:
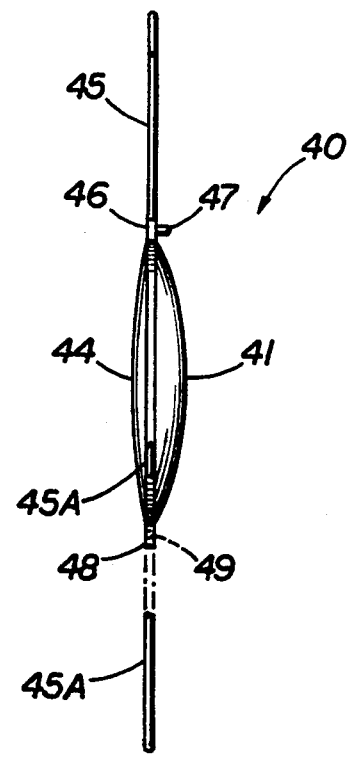
FIG. 5 is a side elevational view of the primary IOL embodiment of FIG. 4.
Figure 6:
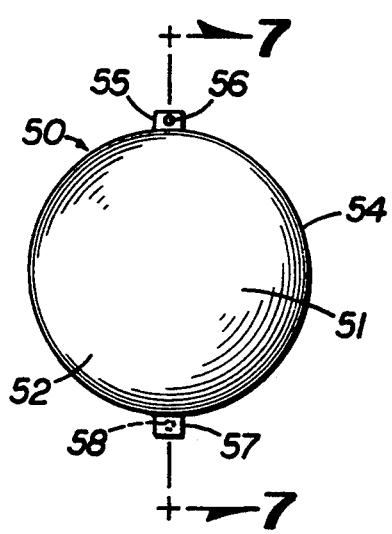
FIG. 6 is a front elevational view of a supplemental IOL for mating with the primary IOL embodiment of FIG. 4 and 5.
Figure 7:
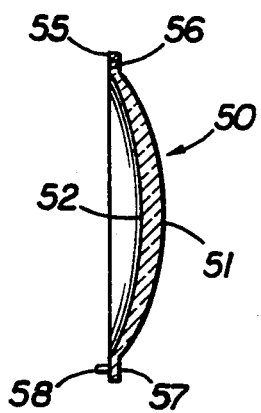
FIG. 7 is a side elevational view of the supplemental IOL embodiment of FIG. 6.
Figure 8:
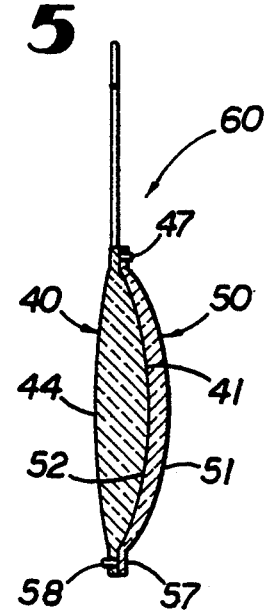
FIG. 8 is a side elevational view of a composite IOL formed by mating the supplemental IOL in FIG. 6 to the primary IOL in FIG. 4.

Referring first to FIGS. 4–8, an SIOL 50 is designed to be mated to a PIOL 40 to form a composite IOL 60, as illustrated in FIG. 8. As seen in FIGS. 4 and 5, the primary IOL 40 is made up of a lens body or optic 42 having a first convex anterior face 41, and a relatively flat posterior face 44. The IOL 40 is substantially circular in cross-section, defined by a continuous peripheral edge 43. There is also included a pair of haptics or support loops 45 and 45a (seen in partial view), projecting outwardly from the edge 43 of optic 42 to support the PIOL 40 in the eye. Although, support loops 45, 45a are configured in what is called a modified J-loop design, the invention can be practiced in conjunction with support loops of any practical shape. The PIOL 40 also includes upper and lower tabs 46 and 48, respectively, that project from the peripheral edge 43 of the optic 42, spaced about 180° apart. In this embodiment, the upper tab 46 includes a post 47 projecting anteriorly (e.g., toward the cornea as shown in FIG. 5) and the lower tab 48 includes a bore 49 for receiving a post 51 on the SIOL 50 similar to the post 47, as discussed below.

Referring to FIGS. 6 and 7, an SIOL 50 is shown, which includes an optic 52 with a convex anterior face 51 and a concave posterior face 53. The curvature of the posterior face 53 is substantially the same as the curvature of the anterior face 41 of the PIOL 40 so they can be mated in contact with each other with no spaces or gaps between them.

As shown in FIG. 6, the SIOL 50 is circular in cross-section defined by continuous peripheral edge 54 and is similar to the shape and size of the PIOL 40, so that they can be placed in juxtaposition as shown in FIG. 8 to form the composite IOL 60. An upper rectangular tab 55 with a bore 56 therethrough for receiving the mounting post 47 of upper tab 46 of PIOL 40, projects from the peripheral edge 54, as does a lower tab 57 that includes a mounting post 58 that projects posteriorly from lower tab 57 to be received into the bore 49 of the lower tab 49 of PIOL 40.

FIG. 8 illustrates the composite IOL 60 which has been formed by the mating of the SIOL 50 to the PIOL 40 through the engagement of upper mounting post 47 of the PIOL 40, in the upper bore 56 of the SIOL 50, and the lower mounting post 58 of the SIOL 50 in the lower bore 49 of the PIOL 40.

In order to form the composite IOL 60 as shown in FIG. 8, and for the other embodiments described below, the radius or radii of curvature of the posterior face of the SIOL should be substantially equal to the radius or radii of curvature of the anterior face of the PIOL. The two solid IOL bodies can be joined to form a solid composite which continuously refracts light without distortion.

By providing an SIOL as described to correct an inaccurately computed diopter power for the PIOL, an incision smaller than the one required for total replacement can be used, involving less trauma to the eye. An added advantage of using the SIOL of the present invention over other known attempts to correct a lens power without removing an originally implanted IOL, is that the SIOL as described can also have a cylindrical or toric optic in addition to spherical ones, to correct astigmatism.

Figure 9:
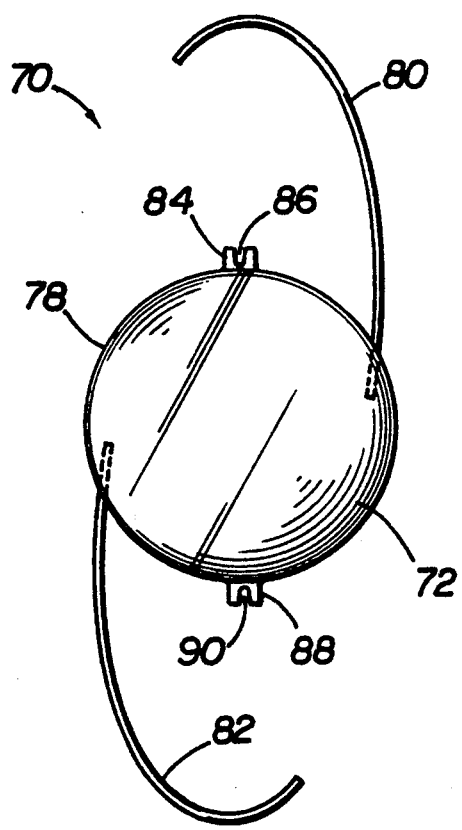
FIG. 9 is a front elevational view of a primary IOL in accordance with a second embodiment of the present invention.
Figure 10:
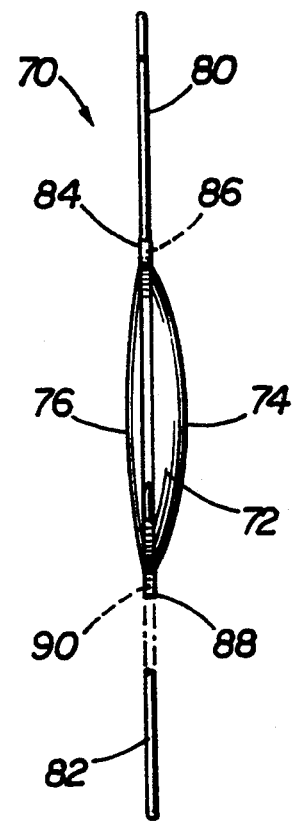
FIG. 10 is a side elevational view of the primary IOL of FIG. 9.

FIGS. 9–12 illustrate another embodiment of the invention, where instead of using posts and bores to mate an SIOL to a PIOL, keys and slots are used. Referring to FIGS. 9 and 10, a PIOL 70 is shown, which includes an optic 72 with an anterior face 74 and a posterior face 76. The optic 72 is defined by a continuous peripheral edge 78 from which project a pair of support loops 80 and 82. A tab 84 is formed integral with the optic 72 and projects outwardly from the peripheral edge 78. A slot 86 is formed in the tab 84. A second tab 88 projects from the edge 78 opposite the tab 84, which also includes a slot 90.

Figure 11:
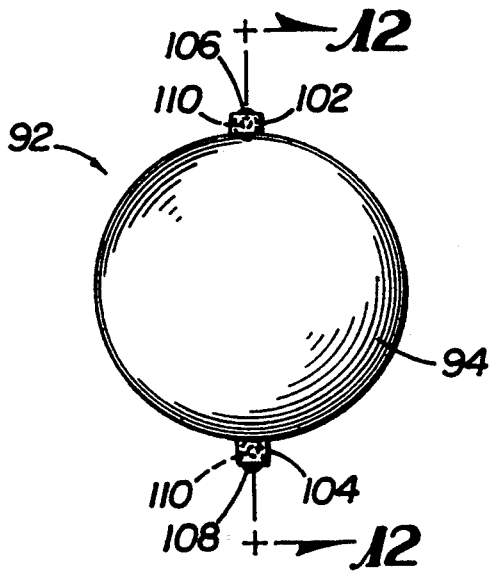
FIG. 11 is a front elevational view of a supplemental IOL for mating with the embodiment of the primary IOL of FIGS. 8 and 9.
Figure 12:
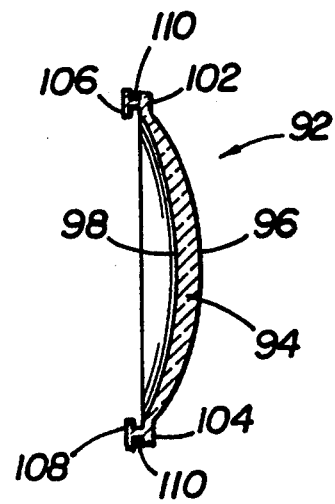
FIG. 12 is a side elevational view of the supplemental IOL of FIG. 11.

FIGS. 11 and 12 show an SIOL 92 with an optic 94 that has an anterior face 96 and a posterior face 98 of substantially the same size and shape as the anterior face 74 of the PIOL 70. The optic 94 has a peripheral edge 100 from which an integral upper tab 102 and an integral lower tab 104 project. The tabs 102, 104 include flange members 106, 108, respectively, that are connected to the tabs through mounting posts 110. In order to form a composite IOL (not shown) similar to the one shown in FIG. 8, the posterior face 98 of the SIOL 92 is mated against the anterior face 74 of PIOL 70, with the flange members 106, 108 engaging the slots 86, 90, respectively.

The SIOL 92 can be formed of one of the so-called "soft" materials mentioned above or of a stiffer plastic such as PMMA. In either case the SIOL 92 would be flexible enough to snap-fit the key members 106, 108 into the slots 86, 90.

Figure 13:
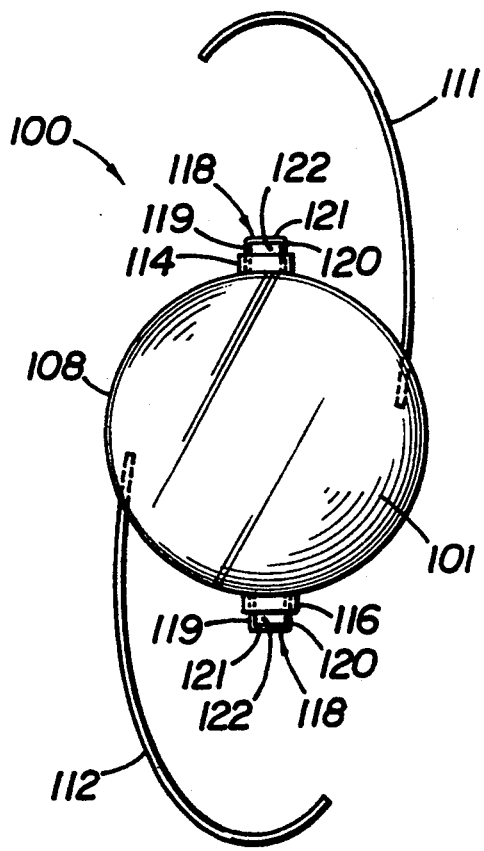
FIG. 13 is a front elevational view of a third embodiment of a primary IOL in accordance with the present invention.
Figure 14:
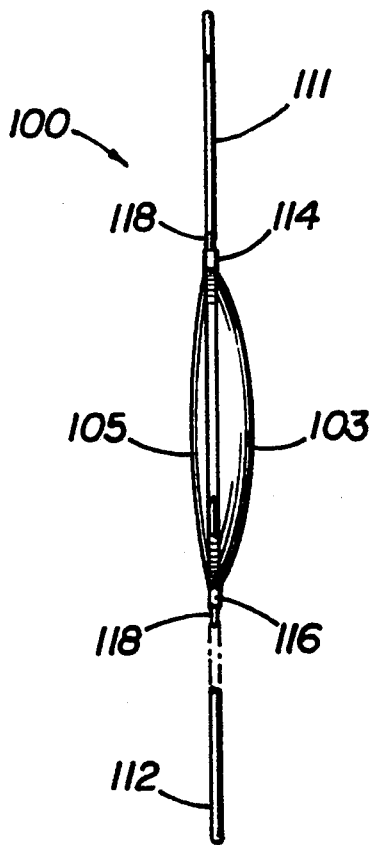
FIG. 14 is a side elevational view of the primary IOL of FIG. 13.

FIGS. 13–16 illustrate another embodiment of the invention where a PIOL 100 has an optic 102 with an anterior face 104, posterior face 106 and a peripheral edge 108. The PIOL 100 also includes support loops 110, 112. As in the embodiments described above, an upper tab 114 and an oppositely-oriented lower tab 116 are integral with and project from the edge 108. In the embodiment of FIGS. 13–14 a U-shaped mounting clip 118 is connected to each tab 114, 116, which includes vertical struts 119, 120 that extend from the tabs 114, 116, respectively, and lateral struts 121 for defining a space 122 surrounded by the struts 114, 116 and 121.

Figure 15:
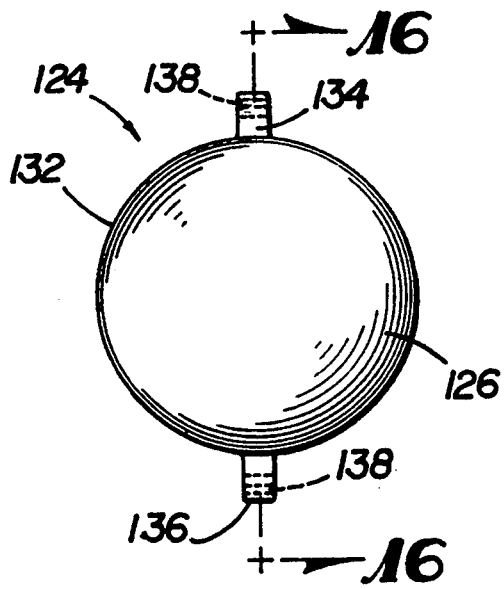
FIG. 15 is a front elevational view of a supplemental IOL for mating with the primary IOL of FIG. 13.
Figure 16:
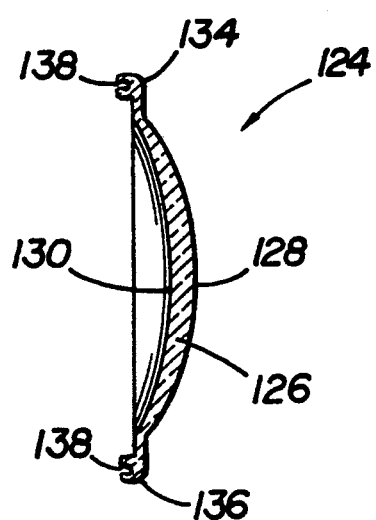
FIG. 16 is a side elevational view of the supplemental IOL of FIG. 15.
Figure 17:
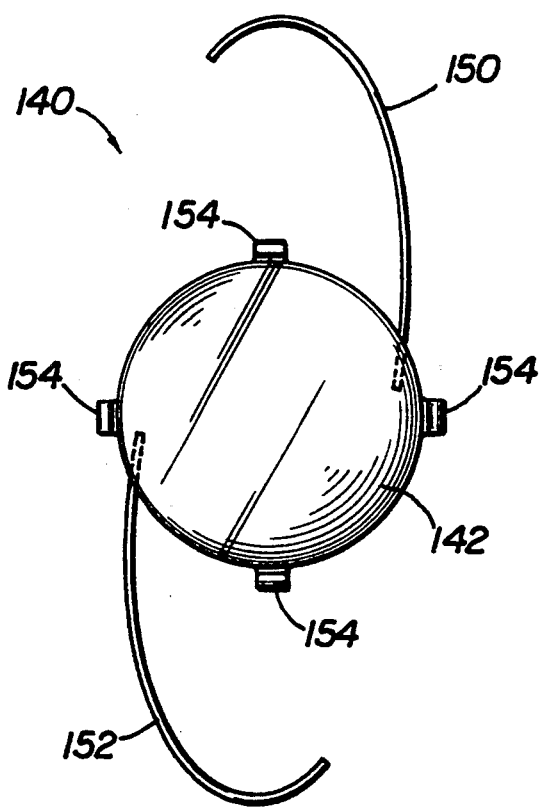
FIG. 17 is a front elevational view of a fourth embodiment of the primary IOL in accordance with the present invention.
Figure 18:
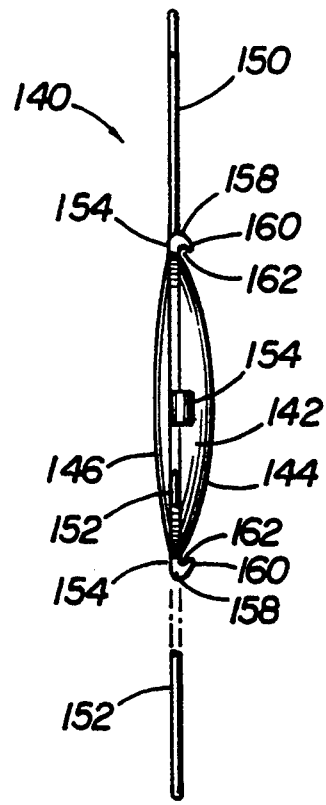
FIG. 18 is a side elevational view of the primary IOL of FIG. 17.
Figure 19:
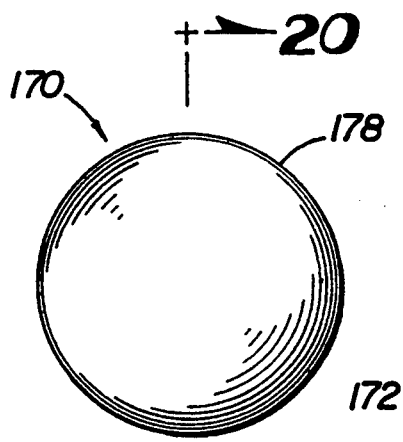
FIG. 19 is a front elevational view of a supplemental IOL for mating with the primary IOL of FIG. 17.
Figure 20:
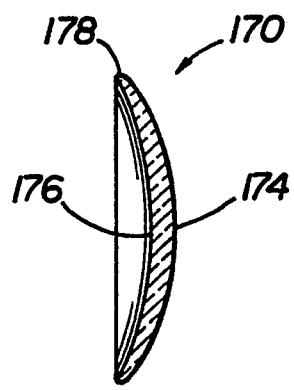
FIG. 20 is a side elevational view of the supplemental IOL of FIG. 19.
Figure 21:
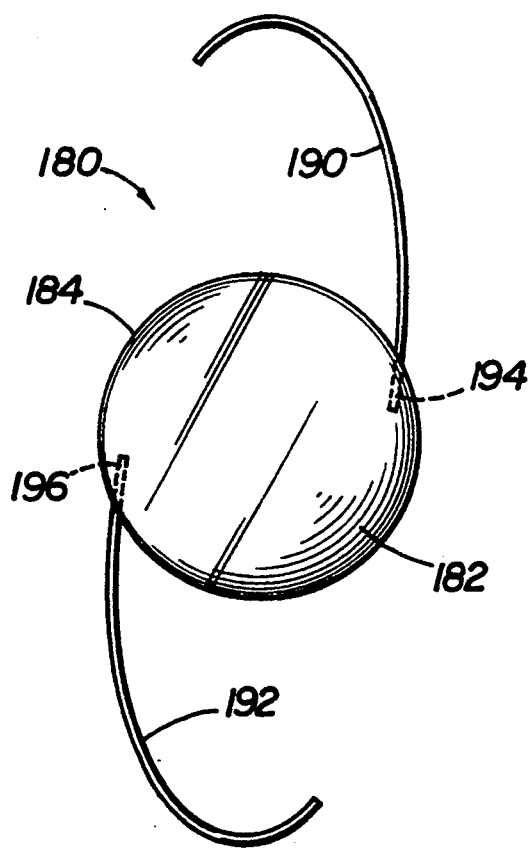
FIG. 21 is a front elevational view of a fifth embodiment of the primary IOL in accordance with the present invention.
Figure 22:
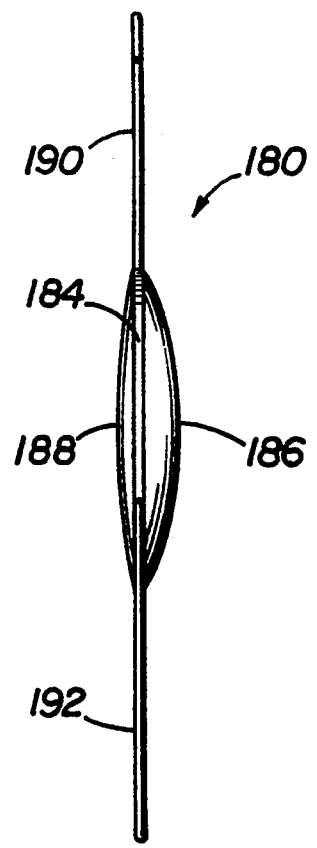
FIG. 22 is a side elevational view of the primary IOL of FIG. 21.
Figure 23:
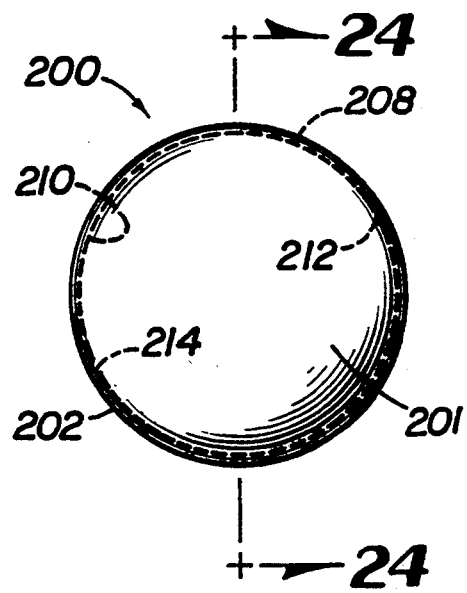
FIG. 23 is a front elevational view of a supplemental IOL for mating with the primary IOL of FIG. 21.
Figure 24:
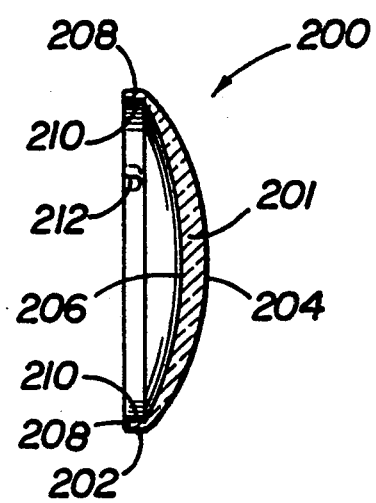
FIG. 24 is a side elevational view of the supplemental IOL of FIG. 23.

FIGS. 15 and 16 show an SIOL 124 with an optic 126 that includes an anterior face 128, a posterior face 130 and a peripheral edge 132. Upper and lower tab members 134, 136 are secured to the peripheral wall 132. The tab members 134, 136 project outwardly from the edge 132 and include open-ended mounting clamps 138 that are shaped and positioned to engage the cross bars 121 of the mounting projections 118 so that a physician can easily mate the SIOL 104 to the PIOL 100 by snapping the clamps 138 onto the cross bars 121 to form a composite IOL (not shown).

FIGS. 17–20 illustrate another embodiment of the present invention where a PIOL 140 includes an optic 142 that has peripheral edge 148, support loops 150, 152, and four spaced-apart, integral mounting tabs 154, that include radially outwardly extending flanges 156 and anteriorly projecting flanges 158 with radially inwardly depending shoulders 160. The flanges 156, 158 and shoulders 160 define receiving spaces 162 for an SIOL 170 of the type shown in FIGS. 19 and 20.

The SIOL 170, unlike those described above, does not include projecting tabs or other protrusions. Instead, a peripheral edge 178 of an optic 172 is shaped to engage the receiving spaces 162. The flanges 156, 158 and shoulder 160 have sufficient memory and stiffness to hold the SIOL 170 in place on the anterior face of the PIOL 140 and form a composite IOL (not shown).

In the embodiment of FIGS. 21-24, there can be seen a primary IOL 180 having an optic 182 portion with a peripheral edge 184. The optic 182 includes an anterior face 186 and a posterior face 188. A pair of loops 190 and 192 are affixed to the lens at attachments 194 and 196. A supplemental IOL 200 includes an optic 201 portion terminating at a peripheral edge 202. The optic includes an anterior face 204 and a posterior face 206. An annular mounting ring 208 communicates with a peripheral edge 202 and can be integral therewith. The annular ring 208 includes an inwardly facing annular mounting surface 210 which registers with the peripheral edge 184 of the primary IOL 180. A pair of circumferentially spaced slots 212 and 214 are formed in the mounting ring 208 so that loops 190 and 192 can register with the slots 212 and 214 respectively when the supplemental IOL 200 is affixed to the primary IOL 180. The supplemental IOL would be affixed to the primary IOL 180 by frictionally engaging the mounting ring 208 to the optic 182 of the primary IOL 180 so that the peripheral edge 184 would frictionally engage the mounting surface 210 of the annular mounting ring 208. In such a configuration, the posterior 206 face of supplemental IOL 200 would register with and abut the anterior face 186 of the primary IOL 180.

Figure 25:
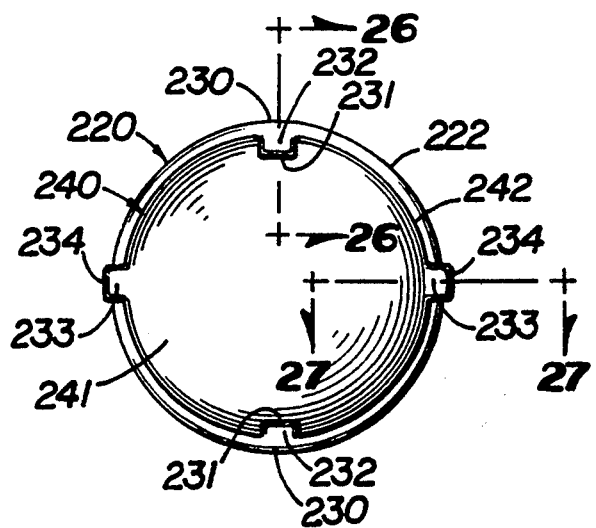
FIG. 25 is a front elevational view of a sixth embodiment of the primary IOL in accordance with the present invention.
Figure 26:
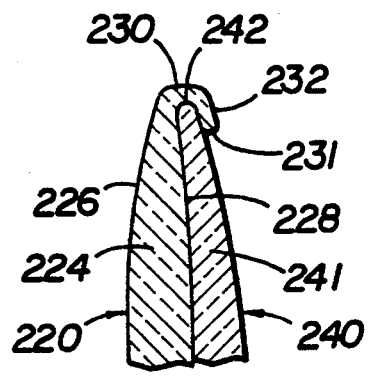
FIG. 26 is a sectional view taken along lines 26—26 of FIG. 25.
Figure 27:
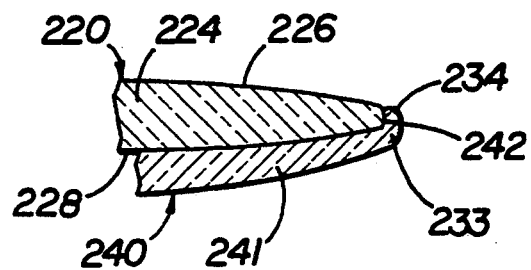
FIG. 27 is a sectional view taken along lines 27—27 of FIG. 25.

In the embodiment of FIGS. 25-27, a primary IOL 220 includes a peripheral edge 222 of an optic 224 which has a posterior face 226 and an anterior face 228. Curved mounting flanges 230 are provided on the primary IOL which include lips 232 terminating at the edges 231. A pair of posterior mounting flanges 233 on the SIOL 240 form lip portions 234. The supplemental IOL 240 includes an optic 241 having a peripheral edge 242 which registers with the mounting flanges 230 as shown in FIGS. 25-27. The anterior face 228 of optic 224 registers with the posterior face 243 of the supplemental IOL 240.

In the embodiment of FIGS. 28-31, there can be seen a primary IOL 250 having a lens optic 252 with a peripheral edge 254. The lens optic 252 has anterior 256 and posterior 258 face portions. A pair of loops 260 and 262 extend from the lens optic 252. A pair of opposed mounting clips 264 are provided extending from the optic 252 peripheral 254. Each clip 264 includes a horizontal strut 265 attached integrally to a pair of vertical struts 266. Each vertical strut 265 attached integrally to a pair of vertical struts 266. Each vertical strut 266 has an end portion 268 which is embedded in the lens optic 252. The clips 264 are preferably circumferentially spaced approximately 180° about the lens periphery 254.

Figure 28:
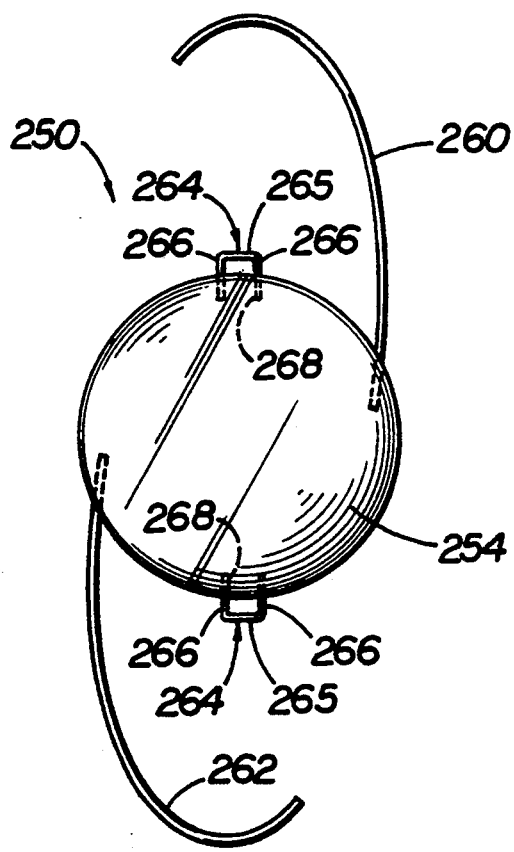
FIG. 28 is a front elevational view of a seventh embodiment of the primary IOL in accordance with the present invention.
Figure 29:
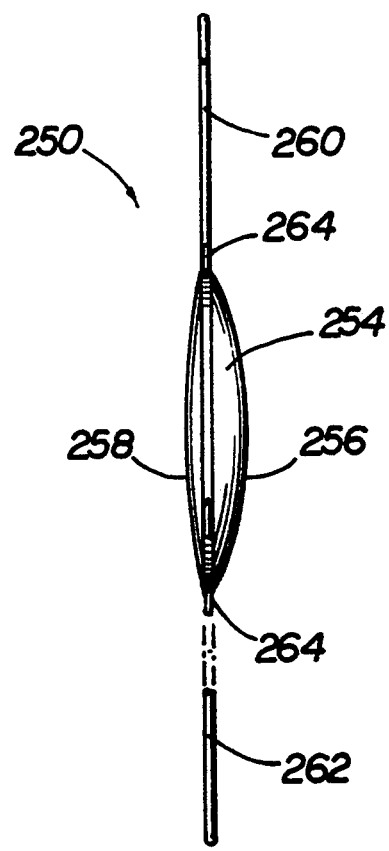
FIG. 29 is a side elevational view of the primary IOL of FIG. 21.
Figure 30:
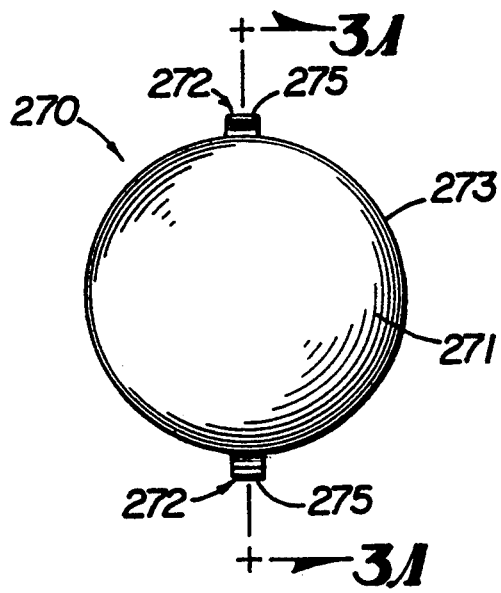
FIG. 30 is a front elevational view of a supplemental IOL for mating with the primary IOL of FIG. 21.
Figure 31:
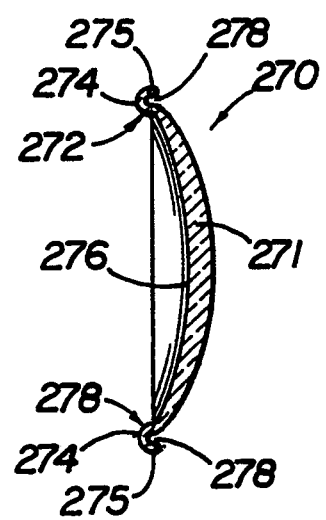
FIG. 31 is a side elevational view of the supplemental IOL of FIG. 23.

In FIGS. 30-31, a supplemental IOL 270 is shown which is connectable to the primary IOL 250 of FIGS. 28-29. Supplemental IOL 270 includes a lens optic 271 having a peripheral edge 273. A pair of mounting flange assemblies 272 are provided and are faced circumferentially about the periphery 273 of optic 271 as shown in FIG. 30. Each mounting flange assembly includes a flange 274 which extends posterior of optic 271 and includes a shoulder 275. The shoulder 275 and flange 274 have sufficient memory and stiffness to engage and retain the clips 264 when optics 252 and 271 are placed against each other so that the posterior surface 276 of supplemental IOL 270 registers upon the anterior surface 256 of primary IOL 250.

In the embodiment of FIGS. 28-31, the optics 252 and 271 could be correspondingly sized. Upon assembly of supplemental IOL 270 upon primary IOL 250, the mounting flange assemblies 272 register with and engage the clips 264. Upon such assembly, the horizontal struts 265 of clips 264 would register with and abut against the shoulder 275 and occupy the recess 278 defined by the shoulder 275 and the posterior flange 274 as shown in FIG. 31.

All of the SIOLs described above could preferably be formed of the "soft" plastics mentioned above so that they can be folded and inserted through a relatively small incision and easily mated with their corresponding PIOLs formed of a stiffer plastic. Alternatively, the PIOLs could be formed of a soft material and the SIOL of a stiffer material or both formed of the soft materials. Both the PIOLs and SIOLs could be formed of stiffer materials such as PMMA so that the SIOLs could easily be mated to the PIOLs through the friction fit connections described above.

Because other embodiments may be made within the scope of the invention, and because many modifications may be made in the embodiments herein described, it is to be understood that the details herein are to be interpreted as being illustrative and not in a limiting sense.

What is claimed as the invention is:

1. A method of changing the refractive power of an intraocular lens, comprising the steps of:
   a. implanting a primary intraocular lens formed of a biocompatible transparent material with a predetermined diopter power;
   b. connecting a supplemental intraocular lens formed of a biocompatible transparent material with a second predetermined diopter power to the primary intraocular lens while the primary lens remains implanted in the eye.

2. The method of claim 1, wherein the step of implanting a primary intraocular lens includes implanting a primary lens without a supplemental intraocular lens.

3. The method of claim 1, wherein the step of implanting a primary intraocular lens includes implanting a primary lens with a first supplemental lens connected to the primary lens and the step of connecting includes connecting a second supplemental lens after removing the first supplemental lens.

4. The method of claim 3, wherein the first supplemental lens has multi-focal characteristics.

5. A method of altering the refractive power of an implanted primary intraocular lens, comprising the steps of:
   a. providing a supplemental intraocular lens formed of a biocompatible transparent material with a predetermined diopter power wherein the predetermined diopter power will alter the refractive power of the implanted primary intraocular lens; and
   b. connecting the supplemental intraocular lens to the implanted primary intraocular lens in situ without removal of said primary intraocular lens.

6. The method of claim 5 wherein the supplemental intraocular lens is formed of a foldable plastic.

7. The invention of claim 5 wherein the supplemental intraocular lens is formed of a relatively stiff plastic.

8. The invention of claim 5 wherein the supplemental intraocular lens has multifocal characteristics.

* * * * *